(12) United States Patent
Matusch (10) Patent No.: US 8,105,271 B2
(45) Date of Patent: Jan. 31, 2012

(54) SINGLE-USE INJECTOR HAVING A FLEXURALLY ELASTIC HOUSING

(75) Inventor: Rudolf Matusch, Marburg (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 13/134,721

(22) Filed: Jun. 15, 2011

(65) Prior Publication Data

US 2011/0251549 A1    Oct. 13, 2011

Related U.S. Application Data

(63) Continuation-in-part of application No. PCT/EP2009/008613, filed on Dec. 3, 2009.

(30) Foreign Application Priority Data

Dec. 18, 2008 (DE) .......................... 10 2008 063 517

(51) Int. Cl.
*A61M 5/30* (2006.01)
(52) U.S. Cl. ......................................................... 604/68
(58) Field of Classification Search ..................... 604/68
See application file for complete search history.

(56) References Cited

U.S. PATENT DOCUMENTS

| | | | | | |
|---|---|---|---|---|---|
| 3,094,989 | A | * | 6/1963 | Stauffer | 604/138 |
| 3,557,784 | A | * | 1/1971 | Shields | 604/68 |
| 5,273,544 | A | * | 12/1993 | van der Wal | 604/134 |
| 5,681,291 | A | | 10/1997 | Galli | |
| 2001/0039394 | A1 | * | 11/2001 | Weston | 604/72 |
| 2001/0051789 | A1 | | 12/2001 | Parsons | |
| 2005/0020984 | A1 | | 1/2005 | Lesch, Jr. | |
| 2006/0264830 | A1 | | 11/2006 | Hommann | |
| 2009/0281496 | A1 | | 11/2009 | Matusch | |
| 2010/0076373 | A1 | | 3/2010 | Matusch | |
| 2010/0106090 | A1 | | 4/2010 | Matusch | |

FOREIGN PATENT DOCUMENTS

| | | |
|---|---|---|
| DE | 84 901 A | 6/1895 |
| DE | 84901 A | 6/1895 |
| DE | 831 756 A | 2/1952 |
| EP | 0 518 416 A1 | 12/1992 |
| FR | 1172205 A | 6/1959 |
| FR | 1290671 A | 4/1962 |
| GB | 805 184 A | 12/1958 |
| GB | 805184 | 12/1958 |
| GB | 805184 A | 12/1958 |
| WO | WO 9624398 A1 | 8/1996 |
| WO | WO 00/62846 | 10/2000 |
| WO | WO 2005/070481 | 8/2005 |

* cited by examiner

*Primary Examiner* — Nicholas Lucchesi
*Assistant Examiner* — Jason Flick
(74) *Attorney, Agent, or Firm* — R. S. Lombard; K. Bach (57) ABSTRACT

A housing of the injector is made from a thin-walled sheet-metal part. The sheet-metal part has at least two branches or legs. Each branch has, at the free end thereof, an angled retaining element or a recess as a means of receiving the cylinder of a cylinder/piston unit. The branches are elastic flexural beams which, in the middle area, are each bent in a Z-shape or S-shape to form a supporting portion for the piston-actuating ram. The contact zone situated between an individual supporting portion and the piston-actuating ram represents a wedge gear pairing that forces the respective branch outwards. The trigger unit comprises at least a trigger element which is slidably supported on the metal sheet, wherein the support section or, respectively the contact sections extend outwardly into longitudinal grooves. The branches may be provided with a locking tongue to engage corresponding openings in the trigger element to lock the housing in position as desired.

20 Claims, 6 Drawing Sheets

SINGLE-USE INJECTOR HAVING A FLEXURALLY ELASTIC HOUSING

CROSS-REFERENCE TO RELATED APPLICATION

This is a continuation-in-part application of pending international application PCT/EP2009/008613 filed Dec. 3, 2009 and claiming the priority of German Application No. 10 2008 063 517.0 filed Dec. 18, 2008.

BACKGROUND OF THE INVENTION

The invention relates to a disposable injector with a housing in which or on which are arranged, in each case at least in some areas, at least one mechanical spring energy reservoir, at least one cylinder/piston unit that can be filled at least temporarily with active substance, at least one piston-actuating ram and at least one trigger unit, wherein the piston-actuating ram is positioned between the spring energy reservoir and the piston of the cylinder/piston unit, wherein the spring energy reservoir comprises at least one pretensioned spring element, wherein the spring-loaded piston-actuating ram is supported on the housing in a releasable manner.

DE 10 2007 031 630 A1 discloses, among other things, an injector of this type. With the exception of the mechanical spring of the spring energy reservoir, almost all the components of the injector are produced expensively from plastics by injection moulding. Components that are subject to high mechanical loads are additionally reinforced with glass fibres.

DE 10 2007 008 369 A1 discloses a one-way injector with a housing in which or on which, in each case at least one cylinder-piston unit which can at least at times be filled with an effective medium, at least one piston operating plunger and at least one trigger unit are arranged, wherein the spring energy store comprises at least one pre-tensioned spring element and wherein at least a part of the piston operating plunger is positioned between the spring-energy store and the piston of the cylinder-piston unit. The spring-charged piston operating plunger includes at least one pull rod which has at least one support surface in the area of its rear end. On the support surface or surfaces locking elements abut the housing whose locking position is secured by a trigger element which is retained in a locking position. The trigger element has a release position which causes the release of the locking elements.

EP 0 518 416 A1 discloses an injection device comprising a glass ampoule with an injection canula and a piston which is slowly pushed into the glass ampoule by a pre-tensioned spring in order to eject the injection liquid contained in the glass ampoule.

Therefore, the problem addressed by the present invention is that of developing a disposable injector of modular design which, with a small overall size, comprises only a small number of components and, while being easy to handle and inexpensive to produce, ensures safe storage and operation.

SUMMARY OF THE INVENTION

This problem is solved by the features of the main claim. Accordingly, the housing of the injector is made from a thin-walled sheet-metal part. The sheet-metal part has at least two branches or legs. Each branch has, at the free end thereof, an angled retaining element or a recess as a means of receiving the cylinder of the cylinder/piston unit. The branches are elastic flexural beams which, in the middle area, are each bent in a Z-shape or S-shape to form a supporting portion for the piston-actuating ram. The contact zone situated between an individual supporting portion and the piston-actuating ram represents a wedge gear pairing that forces the respective branch outwards. The trigger unit comprises at least a trigger element which is slidably supported on the metal sheet, wherein the support section or, respectively the contact sections extend outwardly into longitudinal grooves.

With the invention, a needleless disposable injector, for example, is made available whose piston-actuating ram is released upon triggering of the disposable injector. In order to pretension and hold the spring energy reservoir, the piston-actuating ram is fixed with a form fit via branches on the housing. The branches are surrounded at least in some areas by a trigger element and are held releasably in a locked position before use of the disposable injector. In order to trigger the injector, the branches, which are flexurally elastic at least in some areas, are released transversely with respect to the direction of triggering, such that the piston-actuating ram, under the effect of the spring energy reservoir, can move at least approximately parallel to the centre line of the disposable injector, so as to ensure that the injection solution present in the cylinder of the cylinder/piston unit is discharged via at least one nozzle.

The housing is a simple, thin-walled sheet-metal part, generally just a sheet-metal strip, which supports the mechanical or pneumatic spring of the spring energy reservoir together with a piston-actuating ram and a cylinder/piston unit in cooperation with the trigger element. The punched or cut sheet-metal strip, bent several times, can be produced at very little cost from a ferrous material or a non-ferrous metal. Materials that have a high elastic limit, a high tensile strength and a high yield point are ideal. If appropriate, these can also be high-quality plastics and/or composite materials. Almost any material is suitable, even glass or ceramic.

BRIEF DESCRIPTION OF THE DRAWINGS

Further details of the invention will become clear from the from the following descriptions of a number of illustrative embodiments represented schematically in the drawings, in which.

DETAILED DESCRIPTION OF THE PARTICULAR EMBODIMENTS

Figure 1:
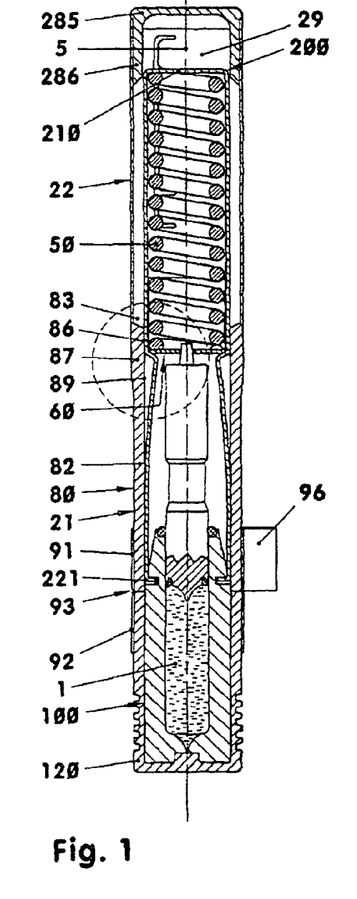
FIG. 1 shows a disposable injector with two flexural branches.

FIG. 1 shows a disposable injector with a permanently charged spring energy reservoir. The disposable injector is composed of a housing (200), which is surrounded by a trigger element (82) and by a protective cap (120), of a cylinder/piston unit (100), which is prefilled with an injection solution for example, of a piston-actuating ram (60), and of a helical compression spring (50) as spring energy reservoir. The cylinder/piston unit (100) lies for the most part in the protective cap (120).

The housing (200) is a sheet-metal strip (201) that has been bent to form a "U". The sheet-metal strip (201), having a width of 18 millimeters for example, is approximately 240 millimeters when flat. The sheet-metal strip (201), produced if appropriate from spring steel, has a wall thickness of 0.5 millimeters, for example. The bent sheet-metal strip (201) is composed of a central end plate (210) and of two flexurally elastic branches (220) protruding at least approximately perpendicularly from the latter. At their free ends, the branches (220), oriented at least in some areas approximately parallel to each other, are each bent inwards at an angle of 90 degrees to form a respective retaining element (221) there. The retaining elements (221) are, for example, 1.5 to 3 millimeters long and protrude towards each other. They form a plane that is oriented parallel to the end plate (210).

Instead of the hook-shaped retaining element (221), each branch (220) can be provided with a recess in which the cylinder of the cylinder/piston unit (100) can be suspended in each case by means of a pin.

Figure 5:
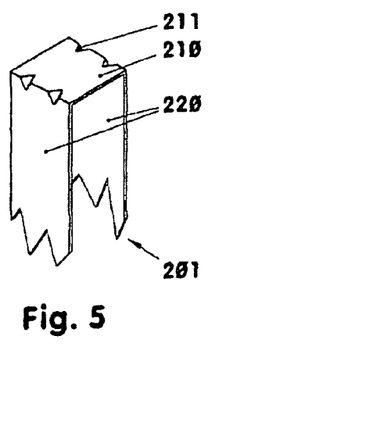
FIG. 5 shows the upper area of the sheet-metal strip.

At the transitions between the end plate (210) and the branches (220), two stiffening beads (211) are in each case pressed in according to FIG. 5. The stiffening beads (211) protrude so far into the end plate (210) that they additionally centre the last winding of the helical compression spring (50) on the end plate (210).

Figure 4:
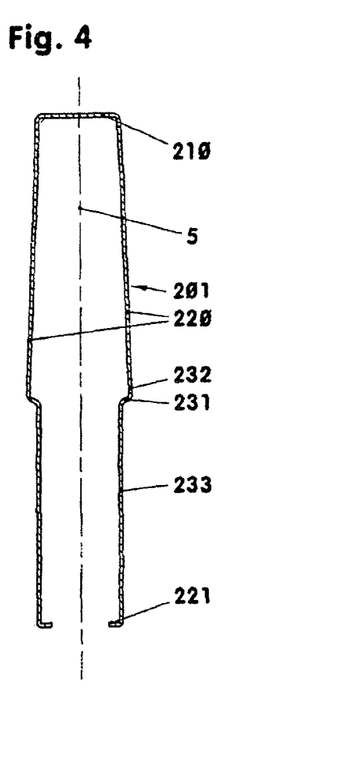
FIG. 4 shows a longitudinal section of the sheet-metal strip.

In the middle area, each branch (220) is bent in a Z-shape or S-shape, the twin-angle bend being mirror-symmetrical to the centre line (5), cf. FIG. 4. In this figure, the sheet-metal strip (201) is shown in the released state. The middle area is in this case a zone which, according to FIG. 4, extends above and below the centre of the housing (200) by approximately a quarter of the total length of the housing.

Each branch (220) is composed of a front retaining portion (233), a central supporting portion (231) and a rear bearing portion (232). The retaining portion (233) is predominantly straight and, according to FIG. 4, extends parallel to the centre line (5). It is adjoined by the relatively short supporting portion (231). The supporting portion (231), measuring approximately 1.5 to 3 millimeters in the longitudinal direction of the sheet-metal strip, cf. FIG. 17, encloses an angle of 112 to 118 degrees, for example, with the retaining portion (233). It is inclined by 65 degrees relative to the vertical.

Figure 10:
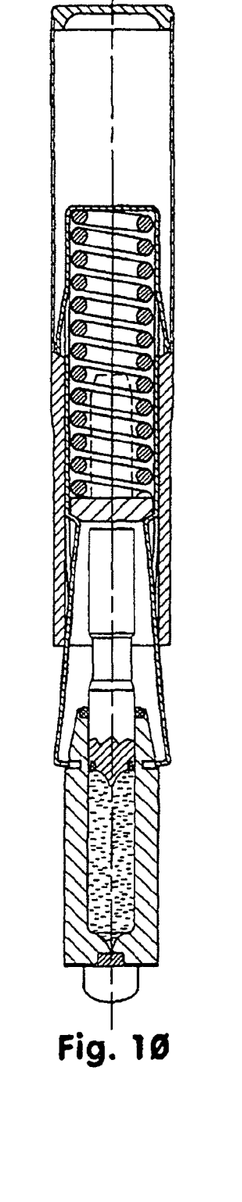
FIG. 10 shows a disposable injector in a simplified design, including a block-shaped ram, in an intermediate assembly stage.

When the disposable injector is in the untriggered state, the piston-actuating ram (60) lies on the supporting portion (231), cf. FIGS. 1 and 10. It is thus under tensile stress.

The supporting portion (231) is adjoined by the bearing portion (232). The latter extends as far as the end plate (210). According to FIG. 4, the bearing portion (232) encloses an angle of 113±3 degrees with the supporting portion (231). According to FIGS. 1 and 6, it lies over a large surface area on the trigger element (82). For example, the trigger element (82) has a ceramic lining in the lower contact zone (86) in which the bearing portion (232) lies over a large surface area when the spring element (50) is tensioned.

According to FIGS. 1, 10, 11 and 17, the piston-actuating ram (60) lies on the supporting portions (231) of the branches (220). The piston-actuating ram (60) is in this case a sheet-metal strip that has been bent in a U-shape and that is composed of a middle part, the ram plate (73), and two guide branches (78). The ram plate (73) is oriented parallel to the end plate (210). The guide branches (78) protrude upwards at a right angle. The helical compression spring (50) sits between the guide branches (78). If appropriate, the guide branches (78) are provided relative to the ram plate (73) with stiffening beads, cf. the stiffening beads (211) of the sheet-metal strip (201) from FIG. 5.

Figure 17:
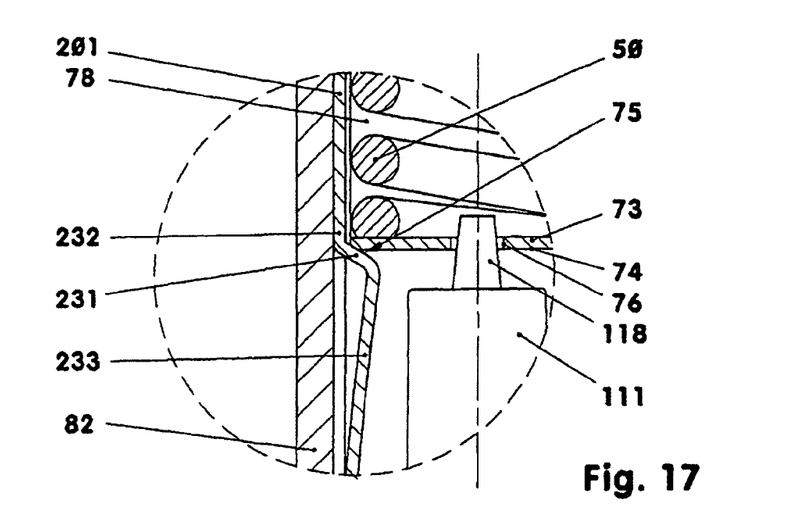
FIG. 17 shows an enlarged detail from FIG. 1.
Figure 18:
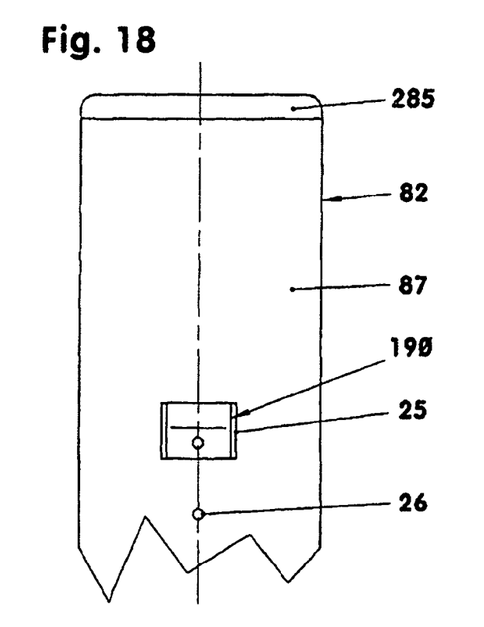
FIG. 18 shows an enlarged side view of FIG. 13.

According to FIG. 17, the ram plate (73), in the area in which it lies on the respective supporting portion (231) of the branch (220), has a 25° bevel (75), for example, in order to ensure contact over a large surface area.

According to FIG. 1, the piston-actuating ram (60) has a width that is slightly smaller, that is to say by ca. 0.1 to 0.3 millimeters, than the normal distance between the two branches (220). Accordingly, the piston-actuating ram (60) is guided laterally on the branches (220). It will be seen in FIG. 2 that the guide branches (78) of the piston-actuating ram (60) are guided with play on the inner wall (89) of the trigger element (82).

According to FIGS. 1 to 3 and 17, among others, the ram plate (73) has a central bore (76) for additionally guiding the rear end of the piston (111) of the cylinder/piston unit (100).

The two tensioned branches (220) hold the piston-actuating ram (60), via the ram plate (73) thereof, in its pretensioned position, cf. FIGS. 1 and 17. For this purpose, the branches (220) bear with their supporting portions (231) on the lower 25° bevel (75) of the ram plate (73). The size of the respective contact surface between the individual supporting portion (231) and the corresponding 25° bevel (75) is in the range of 10 to 30 mm².

The housing (200) made from sheet metal is for the most part surrounded by a trigger element (82) in which it sits and is able to slide. The trigger element (82) is here a square tube which is closed off at the rear end by a lid (285) and which is part of a trigger unit (80). The tube (82) has a front area (21) and a rear area (22).

The front area (21), which relates approximately to the front third of the trigger element (82), has the shape of a square tube with quadratic ring cross section. The four sides walls (87, 88) each have the same wall thickness of 1.5 to 2.5 millimeters in this area (21).

Figure 3:
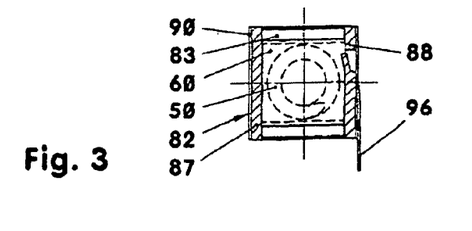
FIG. 3 shows a cross section of FIG. 2.

The rear area (22) has a rectangular ring cross section, cf. FIG. 3, where the side wall (88) is approximately 5 percent wider than the side wall (87). Arranged in parts of the side wall (87) there is a longitudinal groove (83), which extends as far as the rear end of the trigger tube (82). In the area of the longitudinal groove (83), the wall thickness of the side wall (87) is reduced to 0.5 millimeters, for example. The longitudinal groove (83) ends at the front in what is for example a plane return flank (84) which is inclined by approximately 75 degrees relative to the inner wall (89), cf. also FIG. 15. The inclination has the same orientation as the inclination of the supporting portions (231) of the branches (220) of the sheet-metal strip (201).

Figure 9:
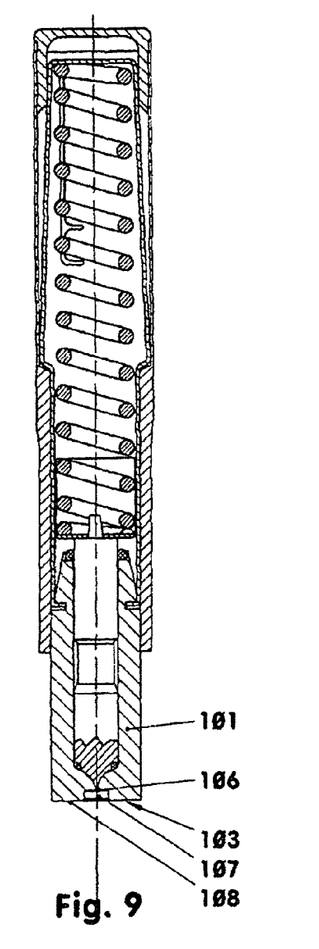
FIG. 9 shows the same as FIG. 1, but in the state when released and actuated.
Figures 11, 13:
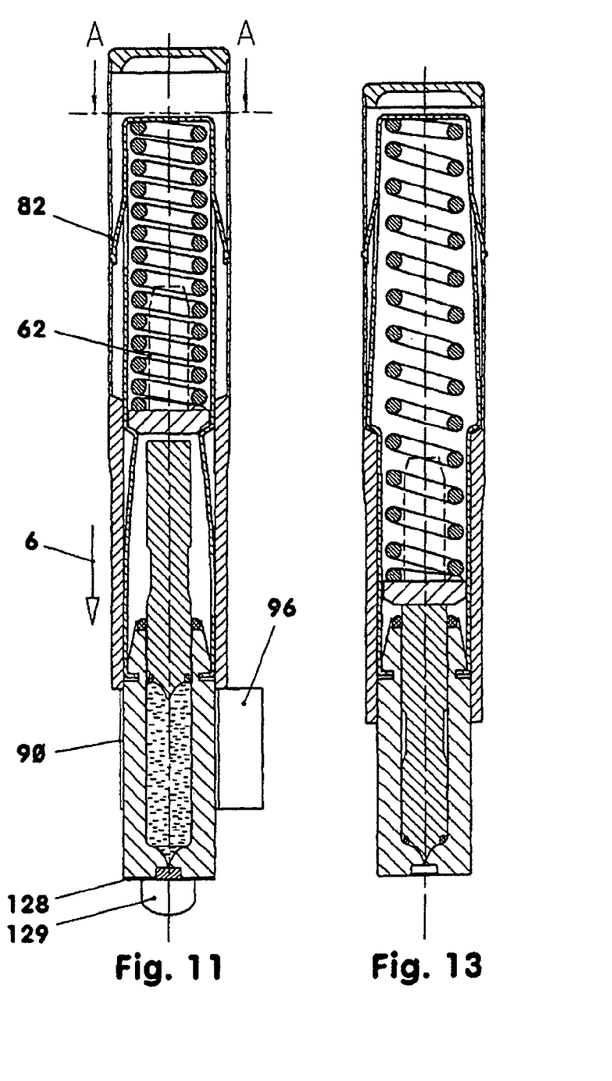
FIG. 11 shows a disposable injector, ready for handling.
FIG. 13 shows the same as FIG. 11, but in the state when released and actuated.
Figure 12:
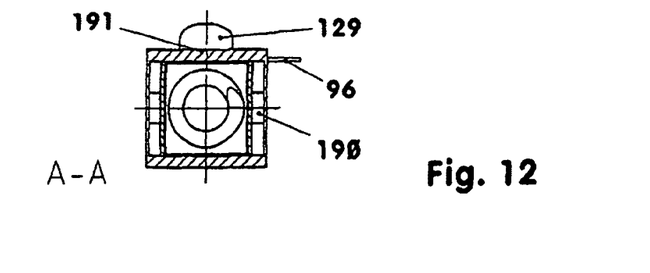
FIG. 12 shows a cross section of FIG. 10.
Figure 16:
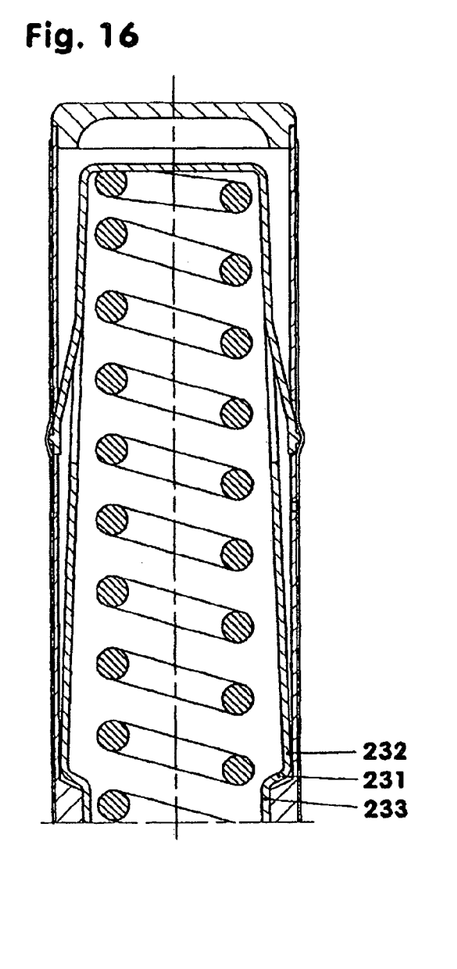
FIG. 16 shows an enlargement of FIG. 13.

When the injector is in the triggered state, the longitudinal groves (83) each receive most of the bearing portion (232) and the supporting portion (231) of the individual branch (220), cf. FIGS. 9, 13, and 16.

Figure 2:
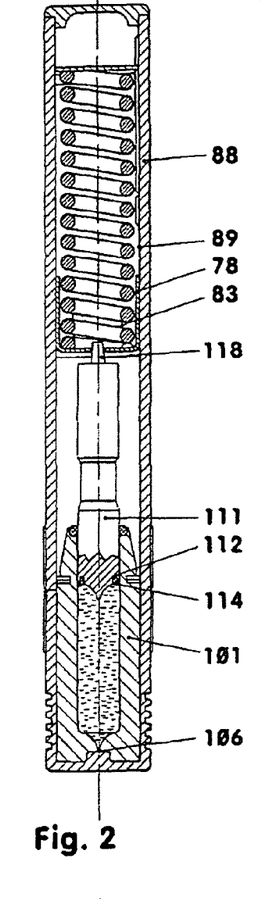
FIG. 2 shows the same as FIG. 1, but pivoted through 90 degrees.
Figure 6:
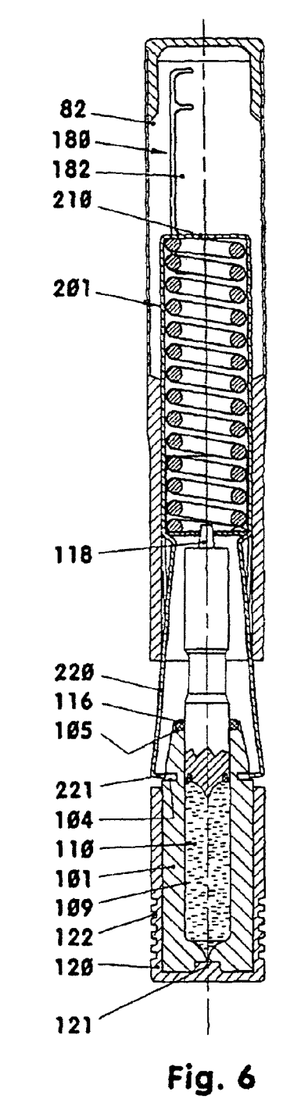
FIG. 6 shows a disposable injector in an intermediate stage of assembly.
Figure 7:
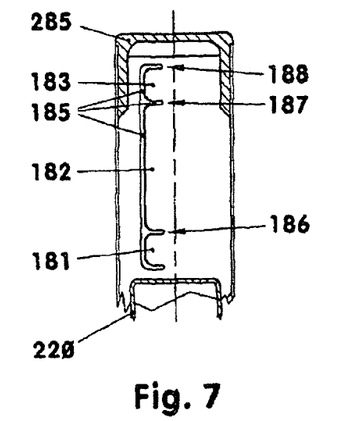
FIG. 7 shows the upper area of the housing during assembly.
Figure 8:
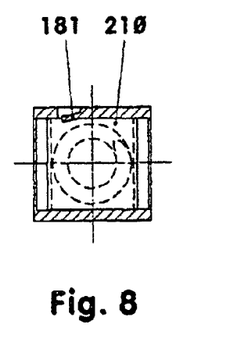
FIG. 8 shows a cross section of FIG. 7.

In the right-hand side wall (88) according to FIG. 2, three elastic locking tabs (181-183) protruding inwards by a few tenths of a millimeters are arranged in the rear area of the trigger tube (82), cf. also FIGS. 6 to 8. The locking tabs (181-183) each have, for example, a rectangular shape. Their wall thickness corresponds to approximately 50% of the wall thickness of the side wall (88). They are delimited on three sides from the wall of the trigger tube (82) and from the nearest locking tab by gaps (185). The gap (185) has a width of 0.5 millimeters, for example. The width corresponds to the wall thickness of the end plate (210). At the locations where two gaps (185) meet each other at right angles, the locking tabs (181-183) are rounded.

The eccentrically arranged locking tabs (181-183), formed integrally on the trigger tube, secure the position of the sheet-metal strip (201) at three locations (186-188). They protrude several tenths of a millimeters into the interior (29) of the trigger element (82). The first location (186) is the gap between the front locking tab (181) and the middle locking tab (182). The end plate (210) is locked in the horizontal gap there, cf. FIG. 6, when the sheet-metal strip (201) is assembled, with the helical compression spring (50) clamped between the piston-actuating ram (60) and the end plate (210), for further intermediate storage.

The second location (187) is the gap between the middle locking tab (182) and the rear locking tab (183). According to FIGS. 1 and 2, the end plate (210) sits here in a disposable injector that has been fully assembled but not yet triggered. The locking of the end plate (210) in this gap prevents withdrawal of the housing (200) from the trigger tube (82), after removal of the protective cap (120). The third location (188) is the gap above the rear locking tab (183). The sheet-metal strip (201) locks itself in this position after the injector has been triggered, cf. FIG. 9. It is secured there against undesired disassembly of the injector that has then been used.

If appropriate, the respective upper corners of the locking tabs (181-183), i.e. the corners facing the lid (285), have a sharp edge, such that the sheet-metal strip (201) can only be pushed into the trigger tube (82). A movement in the opposite direction is then impossible.

In the variant shown above, all the locking elements (181-183) are arranged on the trigger element (82). They fix the position of the end plate (210) relative to the trigger element (82) in some cases temporarily and in some cases permanently. It is also conceivable for the locking elements (181-183) to be replaced by at least one locking element arranged on the housing (200). This element then engages, for example, in corresponding cuttings in the trigger element (82) in order to provide comparable locking positions. A variant of this kind is shown in FIGS. 10 to 16, 18 and 19.

Figure 19:
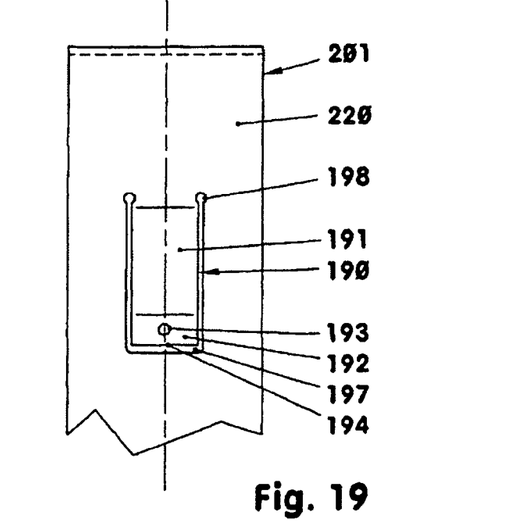
FIG. 19 shows an enlarged side view of the sheet-metal strip from FIG. 10.

For this purpose, a locking tongue (190), with a width of, for example, 6 millimeters, is arranged in the rear quarter, for example, of each branch (220), cf. FIG. 19. The locking tongue (190) is formed by cutting out a U-shaped gap (197), for example, with a width of 0.2 to 0.5 millimeters. In the rear area of the branches (220), that is to say near the end plate (210), the gap (197) ends in bores (198) in order to minimize the notch stresses there. In contrast to the substantially plane bearing portion (232) of the branch (220), the locking tongue (190) is curved several times, cf. also FIGS. 14 to 16. The locking tongue (190) is composed of a flexural portion (191), which deflects resiliently outwards, and of a supporting portion (192). The latter has a locking knob (193) approximately at its centre.

Figure 14:
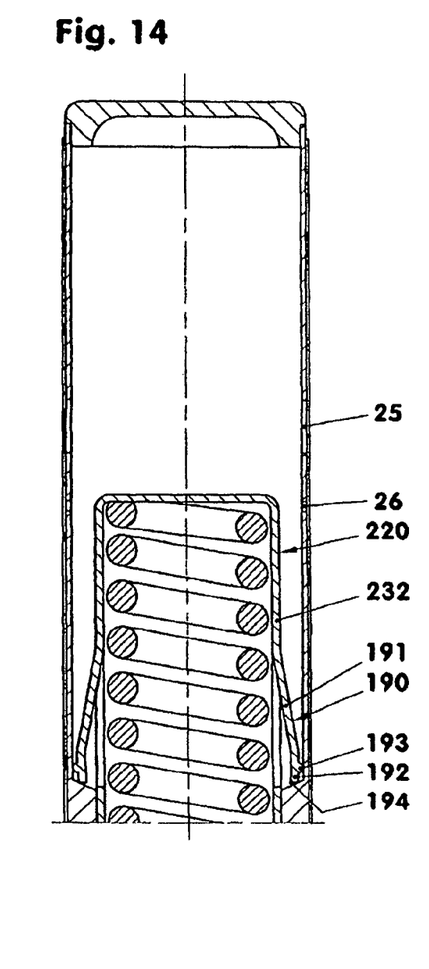
FIG. 14 shows an enlargement of FIG. 10.

In FIGS. 14 and 10, the locking tongue (190) lies in each case with its supporting end face (194) on the return flank (84) of the longitudinal groove (83) of the trigger element (82). In this position, the locking tongue (190) serves as a movement barrier. This corresponds to the first location (186) of the locking mechanism (180) from FIGS. 6 and 7.

Figure 15:
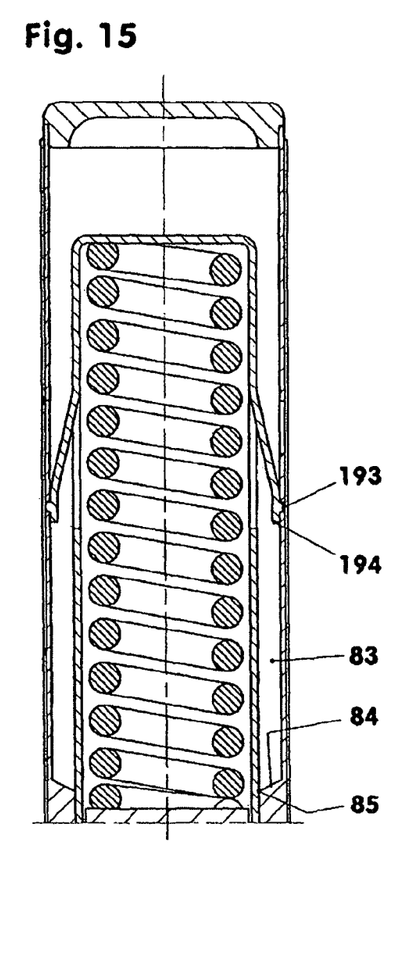
FIG. 15 show an enlargement of FIG. 11.

FIGS. 15 and 11 show the injector in the handling state. The locking knobs (193) of the locking tongue (190) are engaged in the locking bores (26) of the trigger element (82).

After the injector is triggered, the locking tongue (190) engages with its supporting portion (192) in the window (25) of the trigger element (82). The flexural portion (191) in this case lies on the rear edge of the window (25), while the supporting end face (194) bears on the front edge of the window (25). From this locked position, the sheet-metal strip (201) can no longer be pulled forwards out of the trigger tube (82).

When the disposable injector has been fully assembled, the locking recesses (25, 26) and the gaps (185, 197) are covered to protect them from dust, for example by an optionally elastic film which is permanently affixed by adhesive or shrink-fitted and which may, for example, be inscribed.

At the rear end, the trigger tube (82) is closed off by a lid (285). The lid (285) is connected to the trigger element (82), for example, by adhesive bonding, welding, locking or compression. If appropriate, the lid is also formed integrally on the trigger element (82). The lid (285) has two mutually opposite lid tongues (286) which each fill the cross section of the longitudinal grooves (83) of the side walls (87) in the rear area of the trigger tube. The lid tongues (286), which are bevelled towards the interior (29) at their free ends, protrude into the trigger element (82) to such an extent that, according to FIG. 1, they are able to laterally support the sheet-metal strip (201) with slight play in the area of the end plate (210), as long as the injector is in the handling state.

In this illustrative embodiment, the cylinder/piston unit (100) comprises a transparent cylinder (101) which is filled with an injection solution (1) or a solvent, e.g. water for injection, and in which, according to FIG. 1, a piston (111) sits in its rear position.

The cylinder (101) is, for example, a thick-walled pot. The cylinder bore is, for example, cylindrical or frustoconical. In the centre of the bore, of which the cylinder base is adapted at least approximately to the contour of the front end face of the piston (111), there is a short cylindrical, nozzle-like bore (106). The diameter thereof is approximately 0.1 to 0.5 millimeters. This bore (106) is one to five times as long as its diameter. It ends in a cylindrical recess (107) in the outer end face (103) at the bottom of the cylinder (101), cf. FIG. 9. If appropriate, it is also possible to arrange two or more nozzle-like bores (106) in the base of the cylinder (101).

Around the recess (107), an adhesive ring (108) firmly adheres to the end face (103). The adhesive ring (108) covers almost the whole of the end face (103).

The spatial outer contour of the cylinder (101) has, for example, a square configuration in the illustrative embodiment. However, it can also be cylindrical. In the central area of the cylinder, the cross section of the outer contour, oriented transversely with respect to the centre line (5), is a square surface with a central bore. The cross section is dimensioned such that the cylinder (101) slides with slight play in the interior (29) of the trigger tube (82).

In the upper quarter directed towards the trigger tube (82), the cylinder (101) has, in its outer contour, a for example circumferential retaining notch (104) with, for example, a rectangular notch cross section. The hook-shaped retaining elements (221) of the branches (220) engage in the retaining notch (104) in order to fix the cylinder (101) in the injector. Above the retaining notch (104), the cylinder (101) narrows in a truncated pyramid shape. The angle enclosed by mutually opposite pyramidal surfaces is, for example, 20 to 30 degrees. If appropriate, the retaining notch (104) can also be composed simply of two mutually opposite single notches.

The cylinder (101) has a cylinder inner wall (109) which, in the area of the rear face of the cylinder, ends in an annular groove (105) for receiving a sealing element (116).

At its front and at least approximately conically shaped end face, the piston (111) lying in the cylinder (101) has an axial annular groove (112) for receiving a sealing ring (114) or a permanently elastic sealing compound. In its central area, the piston (111) has a waist, and, at its rear end, a central frusto-conical pin (118), which engages with play in the bore (76) of the ram plate (73).

The piston (111) and the sealing element (116) close off the filled interior (110) of the cylinder in a sterile manner.

According to FIG. 11, the cylindrical recess (107) in the bottom end face (103) of the cylinder (101) is closed off by a protective film (128), for example. The protective film (128) adheres over an adhesive ring (108) on the end face (103). It has a lateral pull-off tab (129). In the central area of the protective film (128), there is an elastic stopper which adheres firmly to the protective film (128) and which sealingly fills the hollow space of the recess (107).

As an alternative to this, a pot-shaped protective cap (120) is fitted onto the cylinder (101) from underneath, as shown in FIGS. 1 and 2, among others. In geometrical terms, the one-piece protective cap (120) is composed in principle of five plane walls, and it encloses the cylinder (101) laterally with slight play. In the illustrative embodiment according to FIGS. 1-9, it has the same square-tube cross section as the front area (21) of the trigger tube (82). The upper and, for example, plane end face of the protective cap (120) makes contact with the front end face of the trigger element (82) in the form of a square tube. The outer wall of the protective cap (120) is profiled or structured so as to make it easier to pull off from the cylinder (101). In the illustrative embodiment, a groove profile (122) is used.

The base of the protective cap (120) has a stopper (121) which engages sealingly in the recess (107) of the cylinder (101). The protective cap (120) adheres to the cylinder (101) via the adhesive ring (108). The latter has a substantially greater adherence to the cylinder (101) than it has to the base of the protective cap (120). In order to further ensure the difference in adherence, the base is optionally provided with a profile or a shoulder, such that the contact surface to the adhesive ring (108) is smaller than the contact surface between the adhesive ring (108) and the end face (103) of the cylinder.

The helical compression spring (50) sits pretensioned between the ram plate (73) and the end plate (210) of the sheet-metal strip (201). The spring force is transmitted to the branches (220) via the ram plate (73). Because of the inclination of the bevel (75) of the ram plate (73), the branches (220) are forced radially outwards like a wedge gear, cf. FIG. 17. The bevels (75) make contact with the inclined supporting portions (231) of the branches (220). The bearing portions (232) lie at least virtually flat on the inner wall of the trigger tube (82). The trigger tube (82) thus permanently supports the transverse force caused by the wedge gear.

According to FIGS. 1 and 2, the square-tube-shaped trigger element (82) and the protective cap (120) touch at their end faces. As a tamper-evident seal, this area is additionally enclosed by a banderole (90) as safety element. The banderole (90), which can be torn off or separated, is, for example, a paper strip or film strip that is coated on one side with an adhesive. The film strip surrounds once, for example in a single layer, the combination of trigger element (82) and protective cap (120). It temporarily affixes the parts (82) and (120). To prime the injector or remove the protective cap (120), in preparation for using the injector, the banderole (90) is pulled off or separated in such a way that the adhesive connection between the trigger element (82) and the protective cap (120) is undone. For this purpose, in the illustrative embodiment, the tear-off tab (96) lying in the area of the trigger element (82) is gripped and the banderole (90) is thus wound off, e.g. in sections. In doing so, the banderole (90) tears at a defined and, for example, rectilinear predetermined breaking point (93), which lies exactly in the area of the end faces. Consequently, during priming, only that part (91) of the banderole (90) bearing on the trigger element (82) is removed.

FIGS. 6 and 7 show the injector in an intermediate stage of assembly. The assembly procedure first entails joining the helical compression spring (50) to the piston-actuating ram (60) and the sheet-metal strip (201). To do so, the helical compression spring (50) is fitted into the already shaped sheet-metal strip (201) in such a way that one end of the spring comes to bear on the end plate (210). The stirrup-like piston-actuating ram (60) is pushed onto the other end of the spring. Then, with the aid of an assembly device that guides the helical compression spring (50) on the outside or inside, the sheet-metal strip (201) is pushed together between the end plate (210) and the piston-actuating ram (60), counter to the spring action, to such an extent that the bevels (75) of the end face (74) come to lie behind the supporting portions (231), cf. FIG. 17. In doing so, the bearing portions (232) resting laterally on the piston-actuating ram (60) facilitate the assembly procedure.

The combination of the tensioned spring (50), of the sheet-metal strip (201) and of the piston-actuating ram (60), still tensioned in the assembly device, is now inserted from underneath into the trigger tube (82). The insertion procedure finishes when the end plate (210) locks in the gap (185) situated between the locking tabs (181) and (182). In this position (186), cf. FIG. 6, the free ends of the branches (220) protrude downwards from the trigger tube (82).

In a further assembly stage, the filled cylinder/piston unit (100) is inserted, with the guide pin (118) of the piston (111) to the front, into the trigger tube (82) in such a way that, on the one hand, the guide pin (118) engages in the bore (76) of the piston-actuating ram (60) and, on the other hand, the retaining elements (221) of the branches (220) engage in the retaining notch (104) of the cylinder (101). Starting from this position, the trigger tube (82) is pushed further over the sheet-metal strip (201) until the end plate (210) locks in the gap (185) situated between the locking tabs (182) and (183). In this process, the retaining elements (221) engage securely in the retaining notch (104) and thus fix the cylinder/piston unit (100) in the trigger tube (82). Compared to the assembly stage shown in FIG. 1, all that remains to be done is to apply the tamper-evident seal (90) and cover the longitudinal grooves (83) and the gaps (185) by means of an inscribed film.

FIGS. 10 to 16, 18 and 19 show a variant that differs slightly compared to FIGS. 1 to 9. It differs in seven points, among others. First, the sheet-metal strip (201) has at least one locking tongue (190) per branch (220) to provide lateral centring between the side walls (87) of the trigger tube (82). Second, the piston-actuating ram (60) is just a square plate without a bore and with two or four bevels (75) on its lower end face (74). If appropriate, a guide pin (62), here indicated by broken lines, is secured or integrally formed on the upper end face of the square plate. Third, the piston (111) does not have a guide pin on its rear end face. Fourth, the trigger element (82) has only the locking recesses (25, 26) instead of the locking tabs (181-183), cf. FIG. 7. Fifth, the trigger element (82) has a lid (285) without the lid tongues (286) according to FIG. 1. Sixth, instead of the protective cap (120), cf. FIG. 1, the cylinder (101) only has a protective film (128), cf. FIGS. 10 and 11. Seventh, the banderole (90) is only wound around the cylinder (101). However, the film of the banderole (90) has a sufficient wall thickness to ensure that it securely blocks a movement of the trigger element (82) in the direction of triggering (6).

Figure 20:
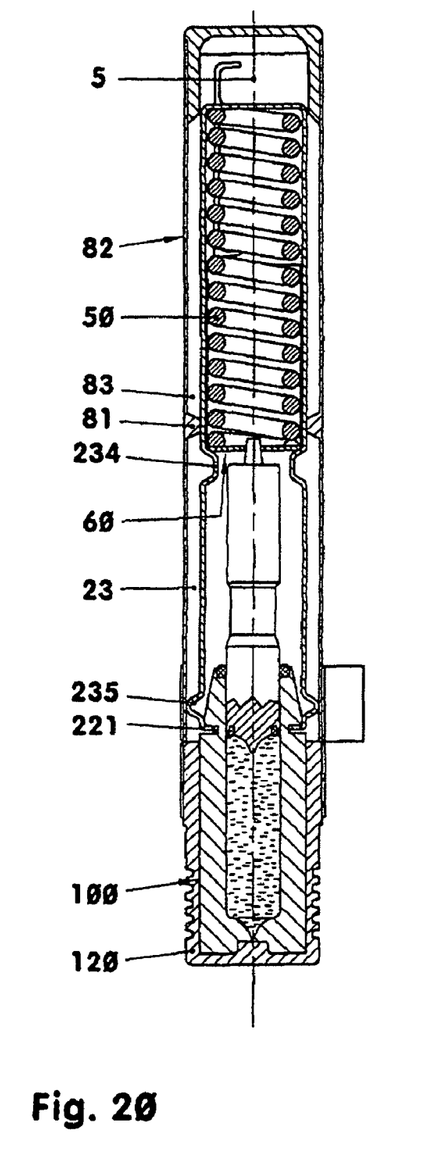
FIG. 20 shows a disposable injector with two multiply bent branches.
Figure 21:
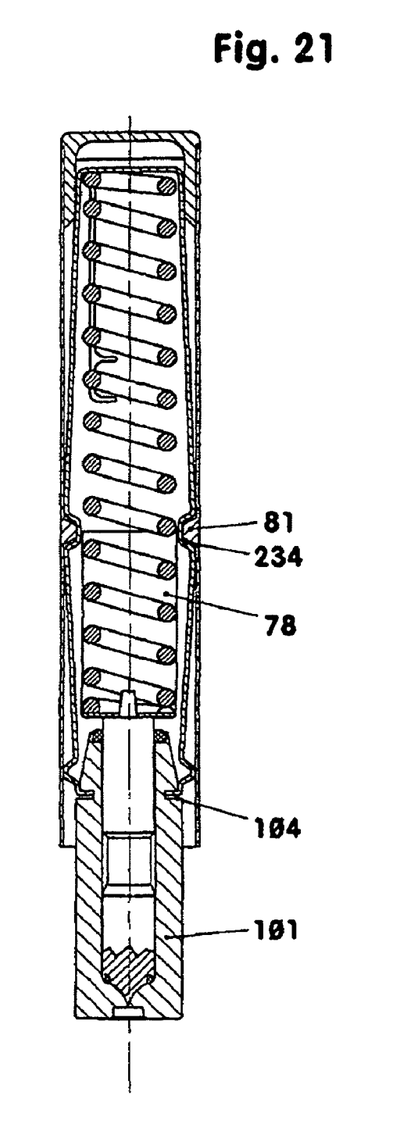
FIG. 21 shows the same as FIG. 20, but in the state when released and actuated.

FIGS. 20 and 21 show an injector whose sheet-metal strip (201) is provided with a locking niche (234) and a guide bulge (235). This sheet-metal strip (201) belongs to a trigger tube (82) which has in each side wall (87) a rear longitudinal groove (83) and a front longitudinal groove (23). The longitudinal grooves (83, 23) are separated from each other by a web (81) which is several millimeters wide and which is arranged more or less centrally in the trigger tube.

The locking niche (234) of the sheet-metal strip (201), the rear area of which is the supporting portion (231), is shaped such that it surrounds the web (81) with play when the injector is triggered, cf. FIG. 21.

The wave-shaped guide bulge (235) is located in proximity to the retaining elements (221). It has the purpose of supporting the front ends of the branches (220) with their retaining elements (221) in such a way that the retaining elements (221) engage safely in the retaining notches (104) of the cylinder (101) in each operating state of the injector.

To prepare the disposable injectors shown in the figures for use, the individual injector is first primed by detaching the tear-off tab (96). The protective cap (120) or the protective film (128) is then withdrawn from the cylinder/piston unit (100). The injector, with the adhesive ring (108) facing forwards, is then positioned on the disinfected injection site. In doing this, the disposable injector is held in the first by way of the trigger tube (82). The thumb of the hand holding the injector rests, for example, on the lid (285), e.g. as when holding a pen.

The trigger tube (82) is now moved in the direction of the cylinder/piston unit (100). In this process, the trigger element (82) slides linearly down the sheet-metal strip (201), that is to say in the direction of the injection site. The bearing portions (232) of the branches (220) slip over the edge (85) and, under the force of the spring element (50), spring outwards in the transverse direction into the longitudinal grooves (83). The supporting portions (231) release the piston-actuating ram (60). The latter shoots downwards unimpeded. In doing so, the end face (74) of the ram plate (73) strikes the end face of the piston (111) previously situated a few tenths of a millimeters or a few millimeters away. The piston (111) forces the injection solution or medicament (1) through the nozzle (106), e.g. initially at $300 \times 10^5$ Pa, until the cylinder (101) is emptied, cf. FIG. 9. The injection procedure is completed with the discharging of the injection solution (1).

The illustrative embodiments show injectors in which the branches (220) of the housing are oriented at least approximately parallel to each other in respective pairs (an angle deviation of ±2 degrees is permissible). The branches (220) lie in parallel planes, wherein the planes, seen in the cross section of the injector, form the mutually opposite sides of a rectangle. The plane of the cross section of the injector lies perpendicular to the centre line (5). These sides can also belong to a rhombus, a parallelogram, a trapezoid or an oblique quadrilateral.

In addition, the branches (220) are each of the same length in respective pairs, and the supporting portions (231) lie opposite each other at the same height, cf. FIGS. 1, 4, 9, etc. This is not absolutely necessary. For example, the supporting portions (231) can lie at different heights if the bearing surfaces of the piston-actuating ram (60) and the return flanks (84) are correspondingly offset.

Instead of the housing (200) being made from a single sheet-metal strip (201), it is also possible for two comparable sheet-metal strips to be combined with each other in a cross. The sheet-metal strips are offset relative to the centre line (5) by an angle of 90 degrees to each other. In this way, for example, the ram plate (73) is enclosed on four sides by the supporting portions (231). This also applies, if appropriate, to the mounting of the cylinder (101).

LIST OF REFERENCE SIGNS 1 injection solution; medicament
5 centre line of injector, longitudinal direction
6 direction of triggering movement of (82), downward movement in direction of arrow
21 front area of (82)
22 rear area of (82)
23 longitudinal groove, front
25 locking window, aperture, locking recess
26 locking bore, locking recess
29 interior of (82)
50 spring element, helical compression spring, spring energy reservoir
60 piston-actuating ram
62 guide pin
73 ram plate
74 end face, lower
75 bevel, 25° bevel
76 bore
78 guide arm
80 trigger unit
81 web
82 trigger element, trigger tube, tube
83 longitudinal grooves, recesses
84 return flank
85 edge, sharp-edged
86 contact zone
87 side wall with longitudinal groove (83)
88 side wall without longitudinal groove (83)
89 inner wall
90 tamper-evident seal, banderole, safety element
91 rear banderole section, on (82); part
92 front banderole section, on (120)
93 predetermined break, perforation
96 tear-off tab
100 cylinder/piston unit
101 cylinder
103 end face
104 retaining notch
105 annular groove
106 bore, nozzle
107 recess in the end face
108 adhesive ring
109 inner wall of cylinder
110 interior of cylinder
111 piston 112 annular groove
114 sealing ring, seal
116 sealing element in (105)
118 guide pin
120 protective cap
121 stopper
122 groove profile
128 protective film, adhesive seal
129 pull-off tab
180 locking mechanism
181 locking tab, front; locking element
182 locking tab, middle; locking element
183 locking tab, rear; locking element
185 gaps
186 1st location
187 2nd location
188 3rd location
190 locking tongue
191 flexural portion
192 supporting portion
193 locking knob
194 supporting end face
197 gap, C-shaped
198 bores
200 housing; sheet-metal part, thin-walled
201 sheet-metal strip; sheet-metal part
210 end plate
211 beads, stiffening beads
220 branch, long and wide, flexural beam
221 retaining elements
231 supporting portion
232 bearing portion
233 retaining portion
234 locking niche
235 guide bulge
285 lid
286 lid tongues

What is claimed is:

1. In combination with a disposable injector with a housing (200) in which or on which are arranged, in each case at least in some areas, at least one mechanical spring energy reservoir (50), at least one cylinder/piston unit (100) that can be filled at least temporarily with active substance, at least one piston-actuating ram (60) and at least one trigger unit (80), the piston-actuating ram (60) is positioned between the spring energy reservoir (50) and the piston (111) of the cylinder/piston unit (100) including a cylinder (101), the spring energy reservoir comprises at least one pretensioned spring element (50), and the spring-loaded piston-actuating ram (60) is supported on the housing (200) in a releasable manner, the improvement which comprises:

the housing (200) is made from a thin-walled sheet-metal part (201), the sheet-metal part (201) has at least two branches (220), the branches (220) each have, at the free ends thereof, an angled retaining element (221) or a recess as a means of receiving the cylinder (101) of the cylinder/piston unit (100), the branches (220) are elastic flexural beams which, in the middle area, are each bent in a Z-shape or S-shape to form a supporting portion (231) for the piston-actuating ram (60), each supporting portion (231) is adjoined by a bearing portion (232), a contact zone situated between the individual supporting portion (231) and the piston-actuating ram (60) represents a wedge gear pairing that forces the respective branch (220) outwards, and the trigger unit (80) comprises at least a trigger element (82) which is slidably supported on the metal sheet part (201), wherein the support portion (231) or, respectively the bearing portions (232) extend outwardly into rear longitudinal grooves (83)

at least one locking tongue (190) arranged on the at least two branches (220), the at least one trigger unit (82) having corresponding openings to received the at least one locking tongue (190) for locking the housing (200) in predetermined position.

2. Disposable injector according to claim 1, wherein the housing (200) is made from a sheet-metal strip (201), and the sheet-metal strip (201) is bent in a U-shape to form two branches (220).

3. Disposable injector according to claim 1, wherein the sheet-metal strip (201) has, at both free ends, inwardly angled retaining elements (221) as a bearing for the piston-actuating ram (60).

4. Disposable injector according to claim 1, wherein the branches (220) are at least five times longer than the width of the branches.

5. Disposable injector according to claim 1, wherein the supporting portion (231) encloses an angle of 115±2 degrees with the portion (233) that carries the respective retaining element (221).

6. Disposable injector according to claim 1, wherein the supporting portion (231) encloses an angle of 113±2 degrees with the portion (232) on which the spring element (50) laterally bears when the injector is tensioned.

7. Disposable injector according to claim 1, wherein the sheet-metal part (201) is made from a spring steel.

8. Disposable injector according to claim 1, wherein the trigger element (82) is a trigger tube surrounding the sheet-metal part (201).

9. Disposable injector according to claim 1, wherein the piston-actuating ram (60) is a flat plate (73) with a rectangular surface area or is made from a sheet-metal strip (73, 78) bent in a U-shape.

10. Disposable injector according to claim 1, wherein the trigger element (82), in combination with the housing (200) and with a tear-off banderole (90) secured thereon, forms a trigger unit (80).

11. Disposable injector according to claim 1, further comprising at least one locking tongue (190) arranged on the at least two branches (220), the at least one trigger unit (82) having corresponding openings to received the at least one locking tongue (190) for locking the housing (200) in predetermined position.

12. Disposable injector according to claim 11, wherein the at least one locking tongue (190) is formed by a U-shaped cut out gap (197) in the at least two branches (220).

13. Disposable injector according to claim 12, wherein the gap (197) ends in bores (198).

14. Disposable injector according to claim 11, wherein the least one locking tongue (190) is curved several times.

15. Disposable injector according to claim 11, wherein the at least one locking tongue (190) is composed of a resiliently outwardly deflecting portion (191) and a supporting portion (192).

16. Disposable injector according to claim 15, wherein the supporting portion (192) has a locking knob (193) proximate the centre thereof and a supporting end face (194).

17. Disposable injector according to claim 16, wherein the trigger element (82) has a locking bore (26) and a locking window (25) in predetermined position for engaging the supporting portion (192).

18. Disposable injector according to claim 1, wherein the at least two branches (220) each include a locking niche (234) and a wave-shaped guide bulge (235).

19. Disposable injector according to claim 18, wherein the at least one trigger element (82) further includes front longitudinal grooves (23) and a web (81) positioned between the rear longitudinal grooves (83) and the front longitudinal grooves (23), the locking niche (234) for engaging the web (81) upon triggering of the injector.

20. Disposable injector according to claim 19, wherein the retaining elements (221) in operative engagement with the cylinder (101), the wave-shaped guide bulge (235) positioned in close proximity to the retaining elements (221) for supporting the branches (220).

* * * * *